US005350584A

United States Patent [19]

McClelland et al.

[11] Patent Number: 5,350,584

[45] Date of Patent: Sep. 27, 1994

[54] SPHERONIZATION PROCESS USING CHARGED RESINS

[75] Inventors: Gregory A. McClelland; Gaylen M. Zentner, both of Lawrence, Kans.

[73] Assignee: Merck & Co., Inc., Rahway, N.J.

[21] Appl. No.: 906,226

[22] Filed: Jun. 26, 1992

[51] Int. Cl.$^5$ .......................... A61K 9/14; A61K 9/18
[52] U.S. Cl. .................... 424/501; 424/78.1; 424/502; 424/78.16
[58] Field of Search .............. 514/951, 772.3, 784, 514/788; 424/78.1, 489, 501, 502, 78.16

[56] References Cited

U.S. PATENT DOCUMENTS

| | | | |
|---|---|---|---|
| 4,808,413 | 2/1989 | Joshi et al. | 424/458 |
| 4,851,421 | 7/1989 | Iwasaki et al. | 514/951 |
| 4,938,967 | 7/1990 | Newton et al. | 424/469 |
| 4,976,949 | 12/1990 | Meyer et al. | 424/497 |
| 5,071,646 | 12/1991 | Malkowska et al. | 514/951 |

FOREIGN PATENT DOCUMENTS

| | | | |
|---|---|---|---|
| 0171528 | 2/1986 | European Pat. Off. | 424/78.1 |
| 717840 | 11/1954 | United Kingdom | 424/78.1 |
| 925890 | 5/1963 | United Kingdom | 424/78.1 |

*Primary Examiner*—Thurman K. Page
*Assistant Examiner*—Peter F. Kulkosky
*Attorney, Agent, or Firm*—Francis P. Bigley; Mark R. Daniel; Joseph F. DiPrima

[57] ABSTRACT

The invention comprises a novel process for the spheronization of charged resins. Spherical multiparticlates are produced which range in size from 0.3 mm to 3 mm in diameter. The spherical particle product is microcrystalline-free. The process consists of the steps of mixing followed by wet granulation, spheronization and drying.

13 Claims, No Drawings

SPHERONIZATION PROCESS USING CHARGED RESINS

FIELD OF THE INVENTION

This invention pertains to both a novel and useful process for preparing spheronized particles from a pharmaceutical formulation containing a charged resin and medicament. These spheronized particles may then be used in the production of drug delivery devices such as those disclosed in U.S. Pat. Nos. 4,795,644; 4,814,183; and 4,976,967.

By incorporating the charged resin, surprisingly, an efficient and simple spheronization process results. In this novel process a medicament is mixed with the charged resin and other pharmaceutical excipients. A wet granulation is prepared from the mixture, which is then extruded through a screen and spheronized. The resultant spherical multiparticulates are dried if necessary.

BACKGROUND OF THE INVENTION

Spheronization has been described as a relatively complex technique in U.S. Pat. No. 5,049,394. This technology, also referred to as marumerization, which means "round maker" was initially described by N. Nakahara (Hicks, D. C. and Freese, H. L., "Extrusion and Spheronizing Equipment, *Pharmaceutical Pelletization Technology*, ed. I. Ghebre-Sellassie, Marcel Dekker, Inc. New York, N.Y., 1989, fn. 1, J. W. Conine and H. R. Hadley, "Preparation of small solid spheres for pharmaceutical use, in updated manuscript, Elanco Products Division, Eli Lilly and Company, Indianapolis, Ind.) The technology affords a process for the combination of drugs and excipients whereby the material to be spheronized is wet granulated and extruded through a screen to produce cylindrical strands of granulation. These strands are then placed on a spheronizer, which is a device which contains a rotating disc. As the strands hit the rotating disc, they tend to fragment. As the strands shorten, they begin to form spheres which are collected and dried.

Other spheronization technology such as high-shear granulation, pan granulation, centrifugal granulation, and rotary fluid-bed granulation has also been employed in the pharmaceutical industry. Each of these techniques have relied on the properties of the microcrystalline celluloses such as AVICEL (TM) to impart the proper plasticity to the material.

Spheronization is complicated by the fact that the granulation must maintain its plasticity during processing or the process will not work. That is, in the spheronization process, the granulation must maintain its malleability and cylindrical form after the extrusion process. Microcrystalline cellulose of various-grades is normally added to the granulation to assure the proper degree of plasticity. Generally, the blend must contain at least 15 to 20% of microcrystalline cellulose in order to remain in a form that is amenable to this process (Gamlen, M. J., Manuf. Chem., June, 1985, p 55 and see also O'Connor, R. E., and Schwartz, J. B., Drug Dev. Ind. Pharm. II, 1837, 1985). However, U.S. Pat. No. 5,049,394 has reported the use of as little as 10% microcrystalline cellulose when an aqueous ethanol solution was used to prepare the granulation.

Often, particularly when the spheronized beads are to be used in certain controlled release dosage forms and processes for medicaments that are incompatible with microcrystalline cellulose, it is necessary to avoid the use of microcrystalline cellulose. Further, it may be advantageous to incorporate inorganic salts, buffers, surfactants or osmotically active agents into the spheres which help to control the localized environment within the spheres in which the medicament will be initially solubilized or otherwise exposed to the fluid in the environment of use.

Surprisingly, it has been found that charged resins may be used in place of microcrystalline cellulose, to impart the desired plasticity for extrusion/spheronization. The procedure results in highly spherical multiparticulates which may be used directly or film coated to produce pharmaceutically useful drug delivery products.

SUMMARY OF THE INVENTION

This invention concerns a novel process for preparing spherical multiparticulates containing charged resins. The charged resin, pharmaceutical excipients and optionally a medicament are dry blended to obtain a uniform mixture of ingredients. The mixture is then wet granulated using water or an aqueous solution of an alcohol or one of the soluble components of the formulation. The resultant wet granulation is extruded through a screen to produce cylindrical strands of granulation needed for the spheronization procedure. The strands are then spheronized to produce spheres which are dried prior to use.

DESCRIPTION OF THE INVENTION

The novel process of this invention concerns the production of spherical multiparticulates using a charged resin, the steps of which comprise:

(a) adding the charged resin and other excipients, optionally including a medicament, to a mixing vessel;

(b) mixing the ingredients to obtain a uniform mixture;

(c) adding a granulating solution;

(d) granulating the mixture until a uniform granulation results;

(e) extruding the wet granulation through a screen to produce strands of granulation;

(f) spheronizing the strands of granulation to produce spherical multiparticulates; and (g) collecting and drying the spherical multiparticulates.

By "spherical multiparticulates" is meant, spherical or near spherical agglomerations of a formulation which range in size from about 0.3 mm to about 3 mm in diameter.

By "charged resin" is meant a polymer with ionizable functional groups that becomes useful in the novel device of this invention. This broadly encompasses any polymer that upon ionization, is capable of producing cationic or anionic polymeric chains and which support spheronization. Typically from about 10% to 70% by weight of the spherical multiparticulate is charged resin.

Illustrative of these charged resins are sodium polystyrene sulfonate which is sold under the trade name AMBERLITE IRP-69 (TM) by Rohm and Haas, Co., Philadelphia, Pa.; the chloride salt of cholestyramine resin USP, sold as AMBERLITE IRP-276 (TM) by Rohm and Haas, Co., Philadelphia, Pa.; the acid form of methacrylic acid-divinyl benzene, sold as AMBER- LITE IRP-64 (TM) by Rohm and Haas Co., Philadelphia, Pa.; carboxypolymethylenes sold under the trade names CARBOPOL 974P and CARBOPOL 934P by B. F. Goodrich, Inc., Brecksville, Ohio, and sodium polyacrylate, sold under the trade name AQUAKEEP J-550 by Seitetsu Kagaku, Japan. In the specification and the accompanying claims, the term "medicament" includes any physiologically or pharmacologically active substance that produces a localized or systemic effect or effects in animals. The term "animal" includes mammals, humans, primates, and domestic, household, sport or farm animals such as sheep, dogs, cats, cattle, horses and pigs, and laboratory animals such as mice, rats and guinea pigs, and fishes, avians, reptiles and zoo animals.

The medicament which can be delivered by the device of this invention includes inorganic and organic compounds without limitation, including drugs that act on the peripheral nerves, adrenergic receptors, cholinergic receptors, nervous system, skeletal muscles, cardiovascular system, smooth muscles, blood circulatory system, synaptic sites, neuroeffector junctional sites, endocrine and hormone systems, immunological system, reproductive system, skeletal systems, autocoid systems, alimentary and excretory systems, inhibitory and histamine systems, and those materials that act on the central nervous system such as hypnotics and sedatives.

Examples of beneficial medicaments are disclosed in *Reminqton's Pharmaceutical Sciences,* 16th Ed., 1980, published by Mack Publishing Co., Eaton, Pa.; and in *The Pharmacological Basis of Therapeutics,* by Goodman and Gilman, 6th Ed., 1980, published by the MacMillan Company, London; and in *The Merck Index,* 11th Edition, 1989, published by Merck & Co., Rahway, N.J. The medicament can be in various forms, such as charged molecules, charged molecular complexes or ionizable salts. Acceptable salts include, but are not limited to hydrochlorides, hydrobromide, sulfate, laurylate, palmitate, phosphate, nitrate, borate, acetate, maleate, malate, succinate, tromethamine, tartrate, oleate, salicylate, salts of metals, and amines or organic cations, for example quaternary ammonium.

Additionally, where appropriate, the medicament may be incorporated into the backbone of a polymer or may be incorporated into the backbone of the charged resin used in the formulation to effect spheronization.

Derivatives of drugs such as esters, ethers and amides without regard to their ionization and solubility characteristics can be used alone or mixed with other drugs. Also, a drug can be used in a form that upon release from the device, is converted by enzymes, hydrolyzed by body pH or other metabolic processes to the parent form, or to a biologically active form.

Specific examples of medicaments which may be adapted for use include,medicaments can be in various forms, such as charged molecules, charged -molecular complexes or ionizable salts. Acceptable salts include, but are not limited to hydrochlorides, hydrobromide, sulfate, laurylate, palmitate, phosphate, nitrate, borate, acetate, maleate, malate, succinate, tromethamine, tartrate, oleate, salicylate, salts of metals, and amines or organic cations, for example quaternary ammonium.

Additionally, where appropriate, the medicament may be incorporated into the backbone of a polymer or may be incorporated into the backbone of the charged resin used in the formulation to effect spheronization.

Derivatives of drugs such as esters, ethers and amides without regard to their ionization and solubility characteristics can be used alone or mixed with other drugs. Also, a drug can be used in a form that upon release from the device, is converted by enzymes, hydrolyzed by body pH or other metabolic processes to the parent form, or to a biologically active form.

Specific examples of medicaments which may be adapted for use include, barbiturates such as pentobarbital sodium, phenobarbital, secobarbital, thiopental and mixtures thereof; heterocyclic hypnotics such as dioxopiperidines and glutarimides; hypnotics and sedatives such as amides and ureas, exemplified by diethylisovaleramide and $\alpha$-bromoisovaleryl urea; hypnotic and sedative urethanes and disulfanes; psychic energizers such as isocarboxazid, nialamide, imipramine, amitryptyline hydrochloride, pargylene, and protryptyline hydrochloride; tranquilizers such as chloropromazine, promazine, fluphenzaine, reserpine, deserpidine, and meprobamate; benzodiazepines such as diazepam and chlordiazepoxide; anticonvulsants such as primidone, phenytoin, and ethosuximide; muscle relaxants and antiparkinson agents such as mephenesin, methocarbomal, cyclobenzaprine hydrochloride, trihexylphenidyl hydrochloride, levodopa/carbidopa, and biperiden; antihypertensives such as $\alpha$-methyldopa and the pivaloyloxyethyl ester of $\alpha$-methyldopa; calcium channel blockers such as nifedipine, diltiazem hydrochloride, diltiazem malate and verapamil hydrochloride; ACE inhibitors such as enalapril and captopril; analgesics such as morphine sulfate, codeine sulfate, meperidine, and nalorphine; antipyretics and antiinflammatory agents such as aspirin, indomethacin, ibuprofen, sodium indomethacin trihydrate, salicylamide, naproxen, colchicine, fenoprofen, sulindac, diflunisal, diclofenac, indoprofen and sodium salicylamide; local anesthetics such as procaine, lidocaine, tetracaine and dibucaine; antispasmodics and muscle contractants such as atropine, scopolamine, methscopolamine, oxyphenonium, papaverine; prostaglandins such as $PGE_1$, $PGE_2$, $PGF_{2\alpha}$; antimicrobials and antiparasitic agents such as penicillin, tetracycline, oxytetracycline, chlorotetracycline, chloramphenicol, thiabendazole, ivermectin, and sulfonamides; antimalarials such as 4-aminoquinolines, 8-amino-quinolines and pyrimethamine; hormonal and steroidal agents such as dexamethasone, prednisolone, cortisone, cortisol and triamcinolone; androgenic steroids such as methyltestosterone; estrogenic steroids such as $17\alpha$-estradiol, $\alpha$-estradiol, $\beta$-estradiol, estriol, $\alpha$-estradiol 3-benzoate, and 17-ethynyl estradiol-3-methyl ether; progestational steroids such as progesterone; sympathomimetic drugs such as epinephrine, phenylpropanolaminehydrochloride, amphetamine, ephedrine and norepinephrine; hypotensive drugs such as hydralazine; cardiovascular drugs such as procainamide hydrochloride, amyl nitrite, nitroglycerin, dipyridamole, sodium nitrate and mannitol nitrate; diuretics such as chlorothiazide, acetazolamide, methazolamide, hydrochlorothiazide, amiloride hydrochloride and flumethiazide, sodium ethacrynate, and furosemide; antiparasitics such as bephenium, hydroxynaphthoate, dichlorophen and dapsone; antineoplastics such as mechlorethamine, uracil mustard, 5-fluorouracil, 6-thioguanine and procarbazine; $\beta$-blockers such as pindolol, propranolol, metoprolol, oxprenolol, timolol maleate, atenolol; hypoglycemic drugs such as insulin, isophane insulin, protamine zinc insulin suspension, globin zinc insulin, extended insulin zinc suspension, tolbutamide, acetohexamide, tolazamide and chlorpropamide; antiulcer drugs such as cimetidine, ranitidine, famotidine and omeprazole; nutritional agents such as ascorbic acid, niacin, nicotinamide, folic acid, choline, biotin, pantothenic acid; essential amino acids; essential fats; ophthalmic drugs such as timolol maleate, pilocarpine nitrate, pilocarpine hydrochloride, atropine sulfate, scopolamine; electrolytes such as calcium gluconate, calcium lactate, potassium chloride, potassium sulfate, sodium fluoride, ferrous lactate, ferrous gluconate, ferrous sulfate, ferrous fumurate and sodium lactate; and drugs that act on α-adrenergic receptors such as clonidine hydrochloride; analgesic drugs such as acetaminophen, oxycodone, hydrocodone, and propoxyphene; antihypercholesterolemic drugs such as simvastatin, pravastatin, lovastatin and gemfibrozil; antiinfective drugs such as cefoxitin, cefazolin, cefotaxime, ciprofloxacin, cephalexin, norfloxacin, amprolium, ampicillin, amoxicillin, cefaclor, erythromycin, nitrofurantoin, minocycline, doxycycline, cefadroxil, miconazole, clotrimazole, phenazopyridine, clorsulon, fludalanine, pentizidone, cilastin, phosphonomycin, imipenem; gastrointestinal drugs such as bethanechol, clidinium, dicyclomine, meclizine, prochlorperizine, trimethobenzamide, loperamide, diphenoxylate, and metoclopramide; anticoagulant drugs such as warfarin, phenindione, and anisindione; and other drugs such as trientine, cambendazole, ronidazole, rafoxinide, dactinomycin, asparaginase, nalorphine, rifamycin, carbamezepine, metaraminol bitartrate, allopurinol, probenecid, diethylpropion, dihydrogenated ergot alkaloids, nystatin, pentazocine, phenylpropanolamine, phenylephrine, pseudoephedrine, alendronate, finasteride, trimethoprim, and ivermectin.

The above list of medicaments is not meant to be exhaustive. Many other medicaments will certainly work in the instant invention.

The medicament can be present as a dispersion, particle, granule, or powder. Also, the medicament can be mixed with a binder, dispersant, emulsifier or wetting agent and dyes.

In cases where medicament is included, the medicament may comprise from about 0.01% to about 90% of the sphere weight.

By "pharmaceutical excipient" is meant compounds such as lactose, magnesium stearate, starch, stearic acid, calcium phosphate, glycerol monostearate, sucrose, polyvinylpyrrolidone, gelatin, methylcellulose, sodium carboxymethylcellulose, sorbitol, mannitol, polyethylene glycol and other ingredients commonly utilized as stabilizing agents or to aid in the production of the spheres may also be present.

In order for the resin to maintain the desired degree of ionization, agents which produce an acidic or basic environment during granulation and spheronization may be included within the formulation. Among the groups of compounds that can exert this effect are acids, bases, and the salts of acids and bases such as adipic acid, citric acid, fumaric acid, tartaric acid, succinic acid, sodium carbonaGe, sodium bicarbonate, sodium citrate, sodium acetate, sodium phosphates, potassium phosphates, ammonium phosphate, magnesium oxide, magnesium hydroxide, sodium tartrate, and tromethamine. Certain compounds may be added to the granulation to assure the proper degree of hydration of the charged resin, medicament and excipients. These hydrating agents include sugars such as lactose, sucrose, mannitol, sorbitol, pentaerythritol, glucose and dextrose. Polymers such as polyethylene glycol as well as surfactants and other organic and inorganic salts can also be used to modulate polymer hydration.

The mixing vessel may be of any size and shape compatible with the size of the formulation to be produced. For example, commercially available mixing devices such as planetary mixers, high shear mixers, or twin cone blenders may be used. If relatively small quantities of formulation are to be prepared, a simple mortar and pestle may be sufficient to mix the ingredients. The type of mixing vessel would be apparent to one skilled in the pharmaceutical art.

By "uniform mixture" is meant that the components of the mixture appear to be uniformly dispersed throughout the formulation. The dry ingredients are mixed prior to granulation to assure that a homogenous granulation will result. This mixing process assures adequate distribution of each of the components of the formulation. In general, mixing times of from about 1 minute to about 60 minutes will be adequate. However, shorter and longer mixing times are within the scope of the invention.

By "granulating solvent" is meant a liquid capable of wetting the dry mixture. Liquids resulting in conversion of the dry powder mixture into a wet granulation that supports subsequent extrusion and marumerization are included. Typically, water or aqueous solutions are employed. Alcohols, typically ethanol or isopropanol, may be included with the granulating water to enhance the workability of the granulation. In another embodiment of this invention, one or more of the components of the formulation is first dissolved in water and this solution is used to produce the wet granulation. An active ingredient or an excipient which is present at very low concentration may initially be dissolved or suspended in the granulating solvent to assure more uniform distribution throughout the formulation.

The purpose of the wet granulation step is to assure that a uniform granulation results, which is sufficiently plastic that extrusion and marumerization are possible. By "plastic" or "plasticity" is meant that the material will retain its cylindrical form after extrusion and be malleable enough to be deformed into spheres during the spheronization operation.

The wet granulation is extruded through a screen to produce cylindrical strands. The diameter of the screen openings determines the diameter of the extrudate. Screen sizes from about 0.5 mm to about 3 mm are useful for this process. In the preferred embodiments of this process, screen sizes from about 0.5 mm to about 1.5 mm are useful. Extrusion may be accomplished using a screw extruder, sieve and basket type extruder, roll extruder, ram extruder or any other pharmaceutically acceptable means of producing the cylindrical strands of granulation.

As the strands leave the extruding process, they may either be stored or passed directly into the spheronizer. In the case of a marumerization spheronization process, the spheronization mechanism consists of a vertical hollow cylinder with a horizontal rotating disk or friction plate located inside. The extrudate is broken into short segments which are rolled into spheres on top of the rotating friction plate which spins at from 500 rpm to 2000 rpm.

The spheres may be dried in any pharmaceutically acceptable manner. This may include air drying or the use of heat or a combination of both. Drying may also be accomplished by exposing the spheres to reduced pressure or to dry environments.

The spheres may be coated to produce beads which may be used in tablets, capsules and other pharmaceutical formulations. For example, the spheres may be coated with a water insoluble, permeable, rate controlling microporous wall as described in U.S. Pat. No. 4,795,644 which is herein incorporated by reference. The wall is comprised of (a) polymeric material that is insoluble in the fluids of the environment of intended use (usually water),and (b) other added excipients that will dissolve in the environmental fluids or leach out of the wall. The leached wall is a sponge-like structure composed of numerous open and closed cells that form a discontinuous interwoven network of void spaces when viewed with a scanning electron microscope.

In a similar manner, walls or films of other compositions may be applied to the spheres. For example, soluble polymers or other materials may be applied to mask taste or to assure that the content of the sphere is not bioavailable until it reaches a particular portion of the body.

EXAMPLES

Example 1

Multiparticulates containing the following were prepared as follows:

| Component | Percent w/w |
| --- | --- |
| Simvastatin | 8.7 |
| Disodium Phosphate | 7.0 |
| Monosodium phosphate | 1.7 |
| Sodium dodecyl sulfate | 21.7 |
| Sodium Chloride | 17.4 |
| Povidone 29-32K | 8.7 |
| AMBERLITE IRP-69 (TM) | 34.8 |
| Butylated Hydroxyanisol | 0.0002 |

Approximately 5.75 kg of the above formulation were mixed in a planetary mixer for 15 minutes. The butylated hydroxyanisol was dissolved in 60 cc of ethanol and water was added to bring the final solution to a volume of 133 cc. This solution was added to the planetary mixer over a two (2) minute period. The mixer was then granulated with seven aliquots of 250 cc of water added over a fifteen minute period. The granulation thus formed was extruded through a 1.0 mm screen and aliquots spheronized by marumerization at approximately 1200 rpm for approximately 10 minutes each. The spherical multiparticulates formed were then dried at 50° C. for 24 hours.

Example 2

Multiparticulates comprised of the following are prepared:

| Component | Percent w/w |
| --- | --- |
| AMBERLITE IRP-276 (TM) | 35 |
| Citric acid | 25 |
| Trisodium citrate | 25 |
| Povidone 90K | 5 |
| Lovastatin | 10 |

The components (200 g) are mixed in a planetary mixer for ten minutes. This mixture is granulated with a 3:1 water:ethanol solution (60 ml) and extruded through a 0.9 mm screen. The resultant extrudate is then spheronized by marumerization at 1330 rpm. The spherical multiparticulates thus formed are dried at 40° C. for 36 hours.

Example 3

Multiparticulates were formed from the following:

| Component | Percent w/w |
| --- | --- |
| Sodium dodecyl sulfate | 56 |
| AMBERLITE IRP-64 (TM) | 40 |
| Povidone 90K | 4 |

18 g of Povidone 90K were dissolved in 50 cc of ethanol. The other components (428 g) were combined in a planetary mixer and mixed for 5 minutes. The dissolved Povidone 90K was slowly added and an additional 60 cc of water were added to this mixture to effect granulation. The granulation was then extruded through a 0.5mm screen and spheronized to produce spherical multiparticulates.

Example 4

Multiparticulates were formed from the following:

| Component | Percent w/w |
| --- | --- |
| CARBOPOL 974P TM | 15 |
| Adipic Acid | 65 |
| Lovastatin | 10 |
| Sodium chloride | 10 |

Ten grams of sodium chloride were dissolved in 40 cc of water. The other components (90 g) were blended in a mortar with a pestle. The dissolved sodium chloride was added slowly to the mortar and the mixture vigorously mixed with the pestle. The resultant granulation was extruded through a 1.0 mm screen and spheronized at approximately 1100 rpm until spheronization of the extrudate was complete. The multiparticulates were then dried at 40° C. for 24 hours.

Example 5

The procedures and methods described in Example 4 were followed to form multiparticulates from the following:

| Component | Percent w/w |
| --- | --- |
| AQUA KEEP J-550 | 15 |
| Mannitol | 65 |
| Lovastatin | 10 |
| Sodium Chloride | 10 |

All of the above examples resulted in the formation of spheronized particles which were suitable for use in pharmaceutical preparations.

What is claimed is:

1. A process for the production of microcrystalline cellulose free multiparticulate comprise a medicament and a charged resin, comprising the steps of:
    (a) adding a charged resin and an excipient to a mixing vessel;
    (b) mixing the charged resin and excipient of (a) to obtain a uniform formulation;
    (c) adding a granulating solution to wet the dry mixture of (b);
    (d) granulating the mixture until a uniform, wet granulation results;

(e) extruding the wet granulation of (d) through a screen to produce strands;

(f) spheronizing the strands of (e) to produce microcrystalline cellulose free spherical multiparticulates;

(g) collecting and drying the spherical multiparticulates.

2. The process of claim 1 wherein a medicament is added to the dry ingredients.

3. The process for the production of spherical multiparticulates of claim 1 wherein the charged resin is chosen from the group consisting of sodium polystyrene sulfonate, the chloride salt of cholestyramine resin USP, the acid form of methacrylic acid-divinyl benzene, carboxypolymethylenes prepared from acrylic acid crosslinked with allyl ethers of sucrose or pentaerythritol, and sodium polyacrylate.

4. The process for the production of spherical multiparticulates of claim 1 wherein the medicament is selected from the group consisting of simvastatin, lovastatin, pravastatin, diltiazem, and the pharmaceutically active salts and crystal forms of these compounds.

5. The process for the production of spherical multiparticulates of claim 1 wherein the excipients are osmotically active agents.

6. The process for the production of spherical multiparticulates of claim 5 wherein the osmotically active agents are selected from the group consisting of sodium chloride, sodium dodecyl sulfate, disodium phosphate, monosodium phosphate, citric acid, trisodium citrate, adipic acid, mannitol, sucrose, and lactose.

7. The process for the production of spherical multiparticulates of claim 1 wherein the dry material is mixed from about 1 to about 60 minutes.

8. The process for the production of spherical multiparticulates of claim 1 wherein the mixing is accomplished using a planetary mixer.

9. The process for the production of spherical multiparticulates of claim 1 wherein the granulating solvent is water.

10. The process for the production of spherical multiparticulates of claim 1 wherein the granulating solvent is a mixture of water and ethanol.

11. The process for the production of spherical multiparticulates of claim 1 wherein a component of the formulation is dissolved in the granulating solvent prior to the wet granulation step.

12. The process for the production of spherical multiparticulates of claim 1 wherein the extrusion occurs through a screen having openings of from about 0.5 mm to about 3 mm.

13. The process for the production of spherical multiparticulates of claim 1 wherein the spheronizer comprises a friction plate which rotates at speeds of from about 500 rpm to about 2000 rpm.

* * * * *

UNITED STATES PATENT AND TRADEMARK OFFICE
CERTIFICATE OF CORRECTION

PATENT NO. : 5,350,584
DATED : September 27, 1994
INVENTOR(S) : Gregory A. McClelland et al It is certified that error appears in the above-indentified patent and that said Letters Patent is hereby corrected as shown below:

Column 8, line 59, claim 1, between the words "multiparticulate" and "comprise", please insert the word --which--.

Signed and Sealed this

Seventh Day of February, 1995

Attest:

BRUCE LEHMAN

*Attesting Officer*     *Commissioner of Patents and Trademarks*